(12) United States Patent
Patterson et al.

(10) Patent No.: US 6,310,053 B1
(45) Date of Patent: *Oct. 30, 2001

(54) LONG-ACTING OXYTETRACYCLINE COMPOSITION

(75) Inventors: Alan Patterson, Belfast; Drew Holmes, Bryansford, both of (GB)

(73) Assignee: Norbrook Laboratories Limited, Northern Ireland (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/617,795

(22) Filed: Jul. 17, 2000

Related U.S. Application Data

(63) Continuation-in-part of application No. 09/159,680, filed on Sep. 24, 1998, now Pat. No. 6,110,905, which is a continuation of application No. 08/765,475, filed on Apr. 8, 1997, now abandoned, which is a continuation of application No. PCT/GB95/01583, filed on Jul. 5, 1995.

(51) Int. Cl.$^7$ .................................................. A61K 31/65
(52) U.S. Cl. ........................................... 514/152; 514/153
(58) Field of Search ..................................... 514/152, 153

(56) References Cited

U.S. PATENT DOCUMENTS

| 4,772,460 | 9/1988 | Malook et al. | 514/152 |
| 5,075,295 | 12/1991 | Zupan et al. | 514/152 |

FOREIGN PATENT DOCUMENTS

| A 20 11 793 | 9/1970 | (DE) . |
| A0 038013 | 10/1981 | (EP) . |
| A0 096 942 | 12/1983 | (EP) . |
| A2 081 434 | 12/1971 | (FR) . |

*Primary Examiner*—Jerome D. Goldberg
(74) *Attorney, Agent, or Firm*—Venable; Keith G. Haddaway; John Shannon

(57) ABSTRACT

An injectable composition is described having a higher residual effect with reduced detrimental effects such as pain at injection site, swelling, tissue irritancy or necrosis. The composition contains as active principle a tetracycline compound, either as the free base or a salt thereof with a physiologically acceptable acid, complexed with a substantially equimolar amount of a magnesium compound, and is solubilized in a water miscible solvent system comprising glycerol formal in a an amount of about 40 (v/v); with from about 1% to about 20% (v/v) polyethylene glycol and optionally containing a pH modifier in an amount sufficient to maintain a physiologically acceptable pH. In addition, the composition may further comprise a thickener, such as polyvinyl in an amount of about 10% (w/v). The balance of the composition comprises water.

21 Claims, No Drawings

LONG-ACTING OXYTETRACYCLINE COMPOSITION

This application is a continuation-in-part of application Ser. No. 09/159,680 filed Sep. 24, 1998, now U.S. Pat. No. 6,110,905, which is a continuation of application Ser. No. 08/765,475 filed Jan. 9, 1997, now abandoned.

FIELD OF THE INVENTION

This invention relates to injectable formulations containing tetracycline, particularly oxytetracycline, which exhibit higher residual effect with less of the known detrimental effects such as pain at injection site, swelling, tissue irritancy or necrosis.

BACKGROUND OF THE INVENTION

Preparation of pharmaceutical compositions containing tetracycline, and oxytetracycline in particular, has always presented a challenge due to aqueous solubility constraints which firstly have impact upon composition stability, and secondly upon parenteral administration.

Prior art oxytetracycline compositions have exhibited relatively high viscosity at low temperatures which makes injection difficult, have shown poor stability and suffered limitations on strength of active principle. Thus, considerable research has gone into determining suitable complexing agents and more favorable co-solvents to address these shortcomings. A review of the art suggests that presence of calcium, and especially magnesium the formulation now appears mandatory as a complexing agent and whereas some improvements have been made in stability and delivery by adopting various co-solvent systems, higher concentration loadings and residual effects remain areas in which improvements are needed. This is especially of interest for veterinary purposes where the need is to deliver high effective doses with minimum effort in animal handling and detrimental effect on the animals requiring treatment.

At the current time, prior art so-called "long-acting" oxytetracycline formulations typically contain 200 mg/ml oxytetracycline and are administered at doses of about 20 mg/kg body weight, having activity as determined by residual blood levels of oxytetracycline detectable for up to about four days or so.

Solubility of oxytetracycline in non-aqueous solvents was considered by Eugene Gans and Takeru Higuchi, Journal of the American Pharmaceutical Association, 1957, Vol XLVI, pp. 587–591.

The patent literature in this area is extensive and one could refer to the following patents which are illustrative of the decades of research carried out on formulation of tetracycline compositions:
GB-A-894 619, GB-A-1 131 007, GB-A-1 250 304,
GB-A-1 286 351, GB-A-1 427 882, GB-A-1 494 558,
GB-A-1 508 601, GB-A-1 514 838, GB-A-1 520 197,
GB-A-1 538 903, GB-A-1 563 478, GB-A-1 592 053
GB-A-2 047 097, EP-B-38 103, EP-B-96 942; U.S. Pat. No. 2,516,080,
U.S. Pat. No. 2,980,584, U.S. Pat. No. 2,990,331, U.S. Pat. No. 3,062,717,
U.S. Pat. No. 3,219,529, U.S. Pat. No. 3,557,280, U.S. Pat. No. 3,712,949,
U.S. Pat. No. 3,957,972, U.S. Pat. No. 4,011,313, U.S. Pat. No. 4,018,889,
U.S. Pat. No. 4,020,162, U.S. Pat. No. 4,126,680, U.S. Pat. No, 4,386,083,
U.S. Pat. No. 4,399,127 U.S. Pat. No. 4,772,460, U.S. Pat. No. 4,957,972, and
U.S. Pat. No. 5,075,295.

From these documents it is apparent that a variety of water-dispersible complex-stabilizers or water-miscible co-solvents have been proposed including 2-pyrrolidone, polyvinyl pyrrolidone, polyethylene glycols, caprolactam, 2-piperidone, and glycerol formal (a reaction product of glycerol and formaldehyde) in specific formulations. However, it is by no means clear that the said co-solvents are equally interchangeable nor can the effect of such a change be entirely predictable for a given formulation.

U.S. Pat. No. 4,386,083 proposes use of glycol formal in conjunction with magnesium acetate and magnesium chloride, whilst U.S. Pat. No. 4,772,460 proposes use of N-methylpyrrolidone (1-methyl-2-pyrrolidone) and a soluble magnesium compound. U.S. Pat. No. 5,075,295 is particularly directed to a composition aiming to achieve up to 30% oxytetracycline, which contains polyethylene glycol 400 and magnesium oxide, but examples given only appear to show a capability of achieving up to 25% oxytetracycline and there is to applicant's knowledge no current commercially available product capable of achieving greater than 20%.

An object of this invention is to provide compositions of substantially greater, long acting effect while minimizing to the greatest extent possible the defects observed in previously proposed formulations. In particular, the invention provides for administration of oxytetracycline formulations at doses ranging from 10 to 40 mg/kilogram bodyweight, giving at 30 mg/kg in animals an extended duration of plasma levels against susceptible organisms in excess of 9 days which is a surprising achievement in light of the known prior art.

DESCRIPTION OF THE INVENTION

Accordingly, this invention provides a composition containing as active principle a tetracycline compound, either as the free base or a salt thereof with a physiologically acceptable acid, complexed with a substantially equimolar amount of a magnesium compound, solubilised in a water miscible solvent system comprising, either
(i) a) glycerol formal in an amount of from about 10 to about 50% (v/v); with
b) polyethylene glycol wherein,
  (i) when the polyethylene glycol has a molecular weight of not more than about 200, the polyethylene glycol is present in an amount of from about 1% to about 20% (v/v);
  (ii) when the polyethylene glycol has a molecular weight of not more than about 400, the polyethylene glycol is present in an amount of from about 1% to about 15% (v/v);
  (iii) when the polyethylene glycol has about molecular weight of not more than about 6000, the polyethylene glycol is present in an amount of from about 1% to about 10% (v/v); and
  (iv) when the polyethylene glycol has a molecular weight of greater than about 6000, the polyethylene glycol is present in an amount of from about 1% to about 5% (v/v); or
(ii) from about 25 to about 75% v/v of N-methylpyrrolidone, said composition optionally containing a pH modifier in an amount sufficient to maintain a physiochemically acceptable pH, the balance being made up with water q.s.

The composition optionally contains a thickener such as polyvinyl pyrrolidone in an amount of up to 10% w/v, and may contain usual formulation aids or auxiliaries typically used for such formulations. Thus, the composition may contain antioxidants, e.g. sodium formaldehyde sulphoxylate and pH preferred pH range of from about 7.5 to about 9.5, more preferably from about 8.5 to about 9.0.

Preferably the composition contains a magnesium compound such as magnesium oxide or a salt e.g. magnesium chloride.

The preferred compositions contain oxytetracycline as the base or its hydrochloride in an amount of from about 15 to abut 35% w/v, complexed with an equimolar ratio of a magnesium compound, preferably a salt, solubilised in a solvent system comprising polyethylene glycol wherein, (1) when the polyethylene glycol has a molecular weight of not more than about 200, the polyethylene glycol is present in an amount of from about 1% to about 20% (v/v); (2) when the polyethylene glycol has a molecular weight of not more than about 400, the polyethylene glycol is present in an amount of from about 1% to about 15% (v/v) or (3) when the polyethylene glycol has about molecular weight of not more than about 6000, the polyethylene glycol is present in an amount of from about 1% to about 10% (v/v) or (4) when the polyethylene glycol has a molecular weight of greater than about 6000, the polyethylene glycol is present in an amount of from about 1% to about 5% (v/v); and glycerol formal in an amount of from about 10 to about 50% v/v. In particular, the preferred compositions contain about 30% w/v oxytetracycline, about 40% glycerol formal, and polyethylene glycol with a magnesium-containing complexing agent or stabilizer, antioxidant and water making up the balance where the compositions contains between about 1% and about 20% of polyethylene glycol 200: or between about 1% and about 15% (v/v) polyethylene glycol 400 or polyethylene glycol 1500; or between about 1 % and about 10% (Y/Y) polyethylene glycol 800 or polyethylene glycol 6000; or, between about 1% and about 5% (v/v) polyethylene glycol 8000. In these compositions, magnesium oxide is suitably present in an amount of about 2.7% w/v and, as antioxidant, sodium formaldehyde sulphoxylate in an amount of about 0.4% w/v may be used. Thus, according to the present invention there is provided a formulation capable of providing from about 10 to about 40 mg/kg bodyweight consisting of:

| Oxytetracycline | 300 mg |
| Magnesium oxide | 27 mg |
| Sodium formaldehyde sulphoxylate | 4 mg |
| Glycerol formal | 0.4 ml |
| Polyethylene glycol | 0.1 ml |
| Monoethanolamine | q.s. pH 8.6 to 8.8 |
| Water for injections | to 1 ml |

The invention will now be further described by way of non-limiting examples for the purposes of practical illustration only.

An oxytetracycline formulation was prepared according to the procedure indicated below using the following components:

| Active Ingredient - | |
| Oxytetracycline | 30% w/v |
| Excipients - | |
| Magnesium oxide | 2.7% w/v |
| Sodium formaldehyde sulphoxylate | 0.4% w/v |
| Glycerol formal | 40% w/v |

-continued

| Polyethylene glycol | 10% w/v |
| Monoethanolamine | q.s. pH 8.6 to 8.8 |
| Water for injections | to 100% w/v |

A controlled environment having an inert atmosphere was provided within which suitable mixing and temperature controllable heating apparatus was assembled. A nitrogen blanket is considered suitable for this purpose. The above components of the proposed composition were mixed by initially mixing a proportion of the total water with the selected solvents. The sodium formaldehyde sulphoxylate, magnesium oxide and oxytetracycline were added sequentially whilst mixing continuously and maintaining a temperature of approximately 65° C. until all the constituents have dissolved. Thereafter, the composition is cooled to below 30° C. and the pH is adjusted to lie within the range of 8.0 to 9.0, in this case by adding a sufficient amount of monoethanolamine. Finally the volume is made up with water, the pH checked and adjusted if necessary, and the composition is filtered through a 0.2 $\mu$m filter and filled into appropriate containers.

In alternative embodiments, where use of a thickener such as polyvinyl pyrrolidone is called for then it should preferably be added after the sodium formaldehyde sulphoxylate.

In order to further investigate the use of polyethylene glycols of varying molecular weights in the formulations according to the invention, a set of experiments was carried out using the general formulation described below prepared as above:

| Oxytetracycline | 300 mg |
| Magnesium Oxide | 27 mg |
| Sodium Formaldehyde Sulphoxylate | 4 mg |
| Glycerol Formal | 0.4 ml |
| Polyethylene Glycol | (as shown in Table 3) |
| Monoethanolamine | q.s. pH 8.6 to 8.8 |
| Water for injections | to 1 ml |

The amount of polyethylene glycol used in the various molecular weight ranges and the results achieved with the various formulations are shown in Table 3.

It will be appreciated that the molecular weights shown for the various designations in polyethylene glycol are approximate. For example, the compound designated PEG 400 typically contains polyethylene glycol having a molecular weight range from about 380 to about 420. It is further noted that PEG 400 and PEG 800 are liquids at room temperature whereas PEG 1500, PEG 6000 and PEG 8000 are solids at room temperature.

It can be seen from the table that PEG 400 is too viscous when used at concentrations of approximately 20% (v/v) or above. Thus, a maximum preferred concentration of PEG 400 is approximately 15%. For polyethylene glycols having a molecular weights between about 800 and about 6,000, formulations containing up to about 10% (v/v) are, although PEG 1500, when present in an amount of about 15% (v/v) gives acceptable results. Finally, for polyethylene glycols having a molecular weight of greater than about 6,000 the preferred amount of polyethylene glycol is not more than about 5%.

The following Tables provide details of Examples 1 to 28 each of which achieved the desired dosage levels and long acting effect.

TABLE 1

| INGREDIENTS | EXAMPLE | | | | | | | | | |
|---|---|---|---|---|---|---|---|---|---|---|
| | 1 | 2 | 3 | 4 | 5 | 6 | 7 | 8 | 9 | 10 |
| Oxytetracycline (% w/v) | 30.0 | 30.0 | 30.0 | 30.0 | 30.0 | 30.0 | 30.0 | 30.0 | 15.0 | 35.0 |
| Magnesium Oxide (% w/v) | 2.7 | 2.7 | 2.7 | 2.7 | 2.7 | 2.7 | 2.7 | 13.25* | 1.3 | 3.0 |
| Sodium Formaldehyde Sulpoxylate (% w/v) | 0.4 | 0.4 | 0.4 | 0.4 | 0.4 | 0.4 | 0.4 | 0.5 | 0.4 | 0.4 |
| Glycerol Formal (% v/v) | 30.0 | 30.0 | 30.0 | 35.0 | 35.0 | 35.0 | 40.0 | 40.0 | 40.0 | 40.0 |
| Polyethylene Glycol 200 (% v/v) | 10.0 | 15.0 | 20.0 | 10.0 | 15.0 | 20.0 | 10.0 | 10 | 10.0 | 10.0 |
| Polyvinyl Pyrrolidone K12 (% w/v) | | | 3.0 | | | | | | | |
| Water to (% v/v) | 100 | 100 | 100 | 100 | 100 | 100 | 100 | 100 | 100 | 100 |

TABLE 2

| INGREDIENTS | EXAMPLE | | | |
|---|---|---|---|---|
| | 11 | 12 | 13 | 14 |
| Oxytetracycline (% w/v) | 30 | 30 | 25 | 35 |
| Magnesium Oxide (% w/v) | 2.78 | 2.78 | 2.3 | 3.21 |
| N-Methyl Pyrrolidone | 30.0 | 60.0 | 60.0 | 60.0 |
| Sodium Formaldehyde Sulphoxylate (% w/v) | 0.4 | 0.4 | 0.40 | 0.4 |
| Water to (% v/v) | 100 | 100 | 100 | 100 |

TABLE 3

| Example | PEG Type | % PEG (v/v) | Viscosity* (cps) | Syringability* |
|---|---|---|---|---|
| 15 | 400 | 5 | A | A |
| 16 | 400 | 20 | N | N |
| 17 | 800 | 1 | 43 | A |
| 18 | 800 | 10 | 98 | A |
| 19 | 800 | 15 | N | N |
| 20 | 1500 | 1 | 38 | A |
| 21 | 1500 | 15 | 145 | A |
| 22 | 1500 | 20 | N | N |
| 23 | 6000 | 1 | A | A |
| 24 | 6000 | 10 | 165 | A |
| 25 | 6000 | 15 | 281 | N |
| 26 | 6000 | 20 | N | N |
| 27 | 8000 | 1 | 56 | Y |
| 28 | 8000 | 10 | N | N |

*A = Acceptable
*N = Not Acceptable

The embodiments illustrated and discussed in this specification are intended only to teach those skilled in the art the best way known to the inventors to make and use the invention. Nothing in this specification should be considered as limiting the scope of the present invention. All examples presented are representative and non-limiting. The above-described embodiments of the invention may be modified or varied, and elements added or omitted, without departing from the invention, as appreciated by those skilled in the art in light of the above teachings. It is therefore to be understood that, within the scope of the claims and their equivalents, the invention may be practiced otherwise than as specifically described.

What is claimed is:

1. A composition containing as active principle an amount of a tetracycline compound effective for antibiotic activity, either as the free base or a salt thereof with a physiologically acceptable acid, complexed with a substantially equimolar amount of a magnesium compound, solubilized in a water miscible solvent system comprising, a) glycerol formal in an amount of from about 10 to about 50% (v/v); with
c) polyethylene glycol wherein,
  (i) when the polyethylene glycol hag a molecular weight of not more than about 200, the polyethylene glycol is present in an amount of from about 1% to about 2(0% (v/v);
  (ii) when the polyethylene glycol has a molecular weight of not more than about 400, the polyethylene glycol is present in an amount of from about 1% to about 15% (v/v);
  (iii) when the polyethylene glycol has about molecular weight of not more than about 6000, the polyethylene glycol is present in an amount of from about 1% to about 10% (v/v); and
  (iv) when the polyethylene glycol has a molecular weight of greater than about 6000, the polyethylene glycol is present in an amount of from about 1% to about 5% (v/v), said composition optionally containing a pH modifier in an amount sufficient to maintain a physiologically acceptable pH, the balance being made up with water q.s.

2. The composition of claim 1, wherein the tetracycline compound is present in an amount of from about 15% to about 35% w/v.

3. The composition of claim 1, wherein the tetracycline compound is present in an amount of about 30%.

4. The composition of claim 1, wherein the tetracycline compound is oxytetracycline base or its hydrochloride.

5. The composition according to claim 1, further comprising, as a thickener, polyvinyl pyrrolidone in an amount of up to about 10% (w/v).

6. The composition according to claim 1, wherein the magnesium compound is selected from the group consisting of magnesium oxide, magnesium salts and magnesium chloride.

7. The composition according to claim 1, wherein magnesium oxide is present in an amount of about 2.7% (w/v) and further comprising, as antioxidant, sodium formaldehyde sulphoxylate in an amount of about 0.4% (w/v).

8. The composition according to claim 1, wherein the composition contains about 30% (w/v) oxytetracycline, about 40% glycerol formal, between about 1% and about 20% (v/v) polyethylene glycol 200 with a magnesium containing complexing agent or stabilizer, antioxidant and water making up the balance.

9. The composition according to claim 8, the magnesium-containing complexing agent is magnesium oxide present in an amount of about 2.7% (w/v) and sodium formaldehyde sulphoxylate as an antioxidant in an amount of about 0.4% (w/v).

10. The composition according to claim 1, wherein the composition contains about 30% (w/v) oxytetracycline, about 40% glycerol formal, between about 1% and about 15% (v/v) polyethylene glycol 400 with a magnesium-containing complexing agent or stabilizer, antioxidant and water making up the balance.

11. The composition according to claim 10, wherein the magnesium-containing complexing agent is magnesium oxide present in an amount of about 2.7% (w/v) and sodium formaldehyde sulphoxylate as an antioxidant in an amount of about 0.4% (w/v).

12. The composition according to claim 1, wherein the composition contains about 30% (w/v) oxytetracycline, about 40% glycerol formal, between about 1% and about 10% (v/v) polyethylene glycol 800 with a magnesium-containing complexing agent or stabilizer, antioxidant and water making up the balance.

13. The composition according to claim 12, wherein the magnesium-containing complexing agent is magnesium oxide present in an amount of about 2.7% (w/v) and sodium formaldehyde sulphoxylate as an antioxidant in an amount of about 0.4% (w/v).

14. The composition according to claim 1, wherein the composition contains about 30% (w/v) oxytetracycline, about 40% glycerol formal, between about 1% and about 10% (v/v) polyethylene glycol 1500 with a magnesium-containing complexing agent or stabilizer, antioxidant and water making up the balance.

15. The composition according to claim 14, wherein the magnesium-containing complexing agent is magnesium oxide present in an amount of about 2.7% (w/v) and sodium formaldehyde sulphoxylate as an antioxidant in an amount of about 0.4% (w/v).

16. The composition according to claim 1, wherein the composition contains about 30% (w/v) oxytetracycline, about 40% glycerol formal, between about 1% and about 10% (v/v) polyethylene glycol 6000 with a magnesium-containing complexing agent or stabilizer, antioxidant and water making up the balance.

17. The composition according to claim 16, wherein the magnesium-containing complexing agent is magnesium oxide present in an amount of about 2.7% (w/v) and sodium formaldehyde sulphoxylate as an antioxidant in an amount of about 0.4% (w/v).

18. The composition according to claim 1, wherein the composition contains about 30% (w/v) oxytetracycline, about 40% glycerol formal, between about 1% and about 5% (v/v) polyethylene glycol 8000 with a magnesium-containing complexing agent or stabilizer, antioxidant and water making up the balance.

19. The composition according to claim 18, wherein the magnesium-containing complexing agent is magnesium oxide present in an amount of about 2.7% (w/v) and sodium formaldehyde sulphoxylate as all antioxidant in an amount of about 0.4% (w/v).

20. A composition containing contains about 30% (w/v) oxytetracycline as active principle, complexed with a substantially equimolar amount of a magnesium compound, solubilized in a water miscible solvent system comprising glycerol formal in an amount of about 40 (v/v) with from about 1% to about 15% (v/v) polyethylene glycol 1500, said composition optionally containing a pH modifier in an amount sufficient to maintain a physiologically acceptable pH, the balance being made up with water q.s.

21. The composition according to claim 20, wherein the magnesium-containing complexing agent is magnesium oxide present in an amount of about 2.7% (w/v) and sodium formaldehyde sulphoxylate as an antioxidant in an amount of about 0.4% (w/v).

* * * * *